United States Patent
Kim et al.

(10) Patent No.: US 9,744,241 B2
(45) Date of Patent: Aug. 29, 2017

(54) METHOD FOR NUCLEIC ACID DELIVERY USING HYALURONIC ACID

(71) Applicants: Samsung Electronics Co., Ltd., Suwon-si, Gyeonngi-do (KR); RESEARCH & BUSINESS FOUNDATION SUNGKYUNKWAN UNIVERSITY, Suwon-si, Gyeonggi-do (KR)

(72) Inventors: Hyun-Ryoung Kim, Guri-si (KR); Jae Hyung Park, Seoul (KR); Hong Yeol Yoon, Hwaseong-si (KR)

(73) Assignees: SAMSUNG ELECTRONICS CO., LTD., Suwon-si (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 292 days.

(21) Appl. No.: 14/242,568

(22) Filed: Apr. 1, 2014

(65) Prior Publication Data

US 2014/0294752 A1     Oct. 2, 2014

(30) Foreign Application Priority Data

Apr. 1, 2013 (KR) ........................ 10-2013-0035289

(51) Int. Cl.
*A61K 9/00* (2006.01)
*A61K 47/32* (2006.01)
(Continued)

(52) U.S. Cl.
CPC .............. *A61K 47/32* (2013.01); *A61K 9/146* (2013.01); *A61K 9/19* (2013.01); *A61K 47/36* (2013.01);
(Continued)

(58) Field of Classification Search
CPC ..................................................... A61K 47/32
See application file for complete search history.

(56) References Cited

U.S. PATENT DOCUMENTS 5,976,567 A    11/1999  Wheeler et al.
6,815,432 B2   11/2004  Wheeler et al.
               (Continued)

FOREIGN PATENT DOCUMENTS

EP    2405001 A1      1/2012
JP    2011-517279 A   6/2011
               (Continued)

OTHER PUBLICATIONS

Choi et al., "Smart Nanocarrier Based on PEGylated Hyaluronic Acid for Cancer Therapy," *ACS Nano*, 5(11): 8591-8599 (2011).
(Continued)

*Primary Examiner* — Paul Dickinson
(74) *Attorney, Agent, or Firm* — Leydig, Voit & Mayer, Ltd.

(57) ABSTRACT

A hyaluronic acid conjugates including hyaluronic acid, a disulfide bond-containing crosslinking agent, and a cationic, amphiphilic polymer; a hyaluronic acid-nucleic acid complex in which a nucleic acid is bound to the hyaluronic acid conjugate; a composition in which the hyaluronic acid-nucleic acid complexes are crosslinked with each other; a nucleic acid delivery composition including the hyaluronic acid-nucleic acid complex; and a method of nucleic acid delivery using the hyaluronic acid-nucleic acid complex.

10 Claims, 12 Drawing Sheets
(7 of 12 Drawing Sheet(s) Filed in Color)

(51) Int. Cl.
  *A61K 47/36* (2006.01)
  *A61K 9/14* (2006.01)
  *A61K 9/19* (2006.01)
  *C12N 15/88* (2006.01)
  *C12N 15/11* (2006.01)

(52) U.S. Cl.
  CPC ............ *C12N 15/111* (2013.01); *C12N 15/88* (2013.01); *C12N 2310/14* (2013.01); *C12N 2320/32* (2013.01)

(56) References Cited

U.S. PATENT DOCUMENTS

| | | |
|---|---|---|
| 8,389,485 B2 | 3/2013 | Czech et al. |
| 8,513,402 B2 | 8/2013 | Kim et al. |
| 2004/0132235 A1 | 7/2004 | Dahmani et al. |
| 2004/0162235 A1 | 8/2004 | Trubetskoy et al. |
| 2008/0160096 A1 | 7/2008 | Berbely et al. |
| 2009/0226528 A1 | 9/2009 | Czech et al. |
| 2011/0143435 A1* | 6/2011 | Stayton ................ A61K 9/1075 435/375 |
| 2012/0065242 A1 | 3/2012 | Kim et al. |
| 2012/0083455 A1 | 4/2012 | Kim et al. |

FOREIGN PATENT DOCUMENTS

| | | |
|---|---|---|
| KR | 2010-0107300 A | 10/2010 |
| KR | 2010-1179471 | 11/2010 |
| KR | 2011-0128325 A | 11/2011 |
| KR | 2012-0026897 A | 3/2012 |
| KR | 2012-0035498 A | 4/2012 |
| KR | 2012-0047346 A | 5/2012 |
| KR | 2012-0080562 A | 7/2012 |

OTHER PUBLICATIONS

Choi et al., "Theranostic nanoparticles based on PEGylated hyaluronic acid for the diagnosis, therapy and monitoring of colon cancer," *Biomaterials*, 33: 6186-6193 (2012).

Lee et al., "Tumor-Homing Poly-siRNA/Glycol Chitosan Self-Cross-Linked Nanoparticles for Systemic siRNA Delivery in Cancer Treatment," *Angew. Chem Int. Ed.*, 51: 7203-7207 (2012).

Yoon et al., "Tumor-targeting hyaluronic acid nanoparticles for photodynamic imaging and therapy," *Biomaterials*, 33: 3980-3989 (2012).

* cited by examiner

METHOD FOR NUCLEIC ACID DELIVERY USING HYALURONIC ACID

CROSS-REFERENCE TO RELATED APPLICATIONS

This application claims the benefit of Korean Patent Application No. 10-2013-0035289 filed on Apr. 1, 2013 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 781 bytes ASCII (Text) file named "715830_ST25.TXT," created Apr. 1, 2014.

BACKGROUND OF THE INVENTION

1. Field

Provided are hyaluronic acid conjugates, complexes, and compositions useful for nucleic acid delivery. Additionally, the present invention relates to methods for nucleic acid delivery using hyaluronic acid conjugates, complexes, and compositions.

2. Description of the Related Art

Small interfering ribonucleic acid-based (siRNA-based) therapeutics are actively being developed worldwide, and are used for the treatment of incurable diseases such as Alzheimer's disease, diabetes, obesity, rheumatoid arthritis, Parkinson's disease, hepatitis type B, hepatitis type C, AIDS, cancer, and the like. siRNA-based therapeutics are designed to regulate the expression mechanism of their target genes by destroying specific messenger ribonucleic acid (mRNA) to cease the transcription and translation of target genes. However, siRNA is susceptible to degradation by various enzymes that are abundantly found in the blood plasma of living organisms (e.g., mammals), within a short time after the siRNA is exposed to blood. As a result, when siRNAs are injected intravenously, most siRNAs are degraded before they are able to perform their function unless they are biochemically protected. In addition, siRNAs are likely to be recognized as an antigen or a foreign matter in vivo, which may induce an undesirable immune response. Furthermore, siRNA may affect a gene locus other than a target gene, provoking cross-hybridization with irrelevant gene sequences. Accordingly, active research has been conducted to develop new siRNA formulations with enhanced stability and minimized undesirable side effects. Particular attention has been paid to various drug delivery systems including nanoparticles, micelles, liposomes, polymer complexes, etc. to increase in vivo stability of siRNA while minimizing the undesirable side effects of siRNA drugs. Non-viral siRNA drug delivery systems that have been developed attempt to increase the stability of siRNA. These systems bind siRNA to the surface of positively charged liposomes to stabilize the siRNA in an effort to prevent the rapid destruction of siRNA, which is common when isiRNA is administered alone.

Alternative strategies combine siRNA with a positively charged, amphiphilic polymer through electrostatic interaction to form an electrically neutral nanoparticle which is improved in targeting ability, to effectively deliver siRNA to a target. Cancer, representative of the diseases to which siRNA therapy is applicable, is characterized by active cell division, requiring a massive supply of nutrients and oxygen, compared to normal tissues. Cancer tissues form vessels to meet these demanding nutrient and oxygen requirements. The walls of the newly formed vessels are structurally irregular and flimsy. In addition, cancer tissues experience significantly lower drainage through the lymphatic duct than compared to normal tissues. As a result, polymers can be retained longer in cancer tissues than other tissues or organs. To take advantage of the enhanced permeability and retention (EPR) characteristics of cancer, amphiphilic nanoparticle-siRNA complexes have recently been suggested for effective delivery of siRNA.

Nonetheless, there still is a need for a delivery system by which nucleic acids can be delivered at greater efficiency with higher stability to a subject.

SUMMARY

Provided is a hyaluronic acid conjugate including hyaluronic acid, a sulfur-containing crosslinking agent, and a cationic, amphiphilic polymer. Additionally, provided is a hyaluronic acid-nucleic acid complex, wherein a hyaluronic acid conjugate according to an embodiment and a nucleic acid are coupled. Related conjugates, compositions, methods, and complexes also are provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
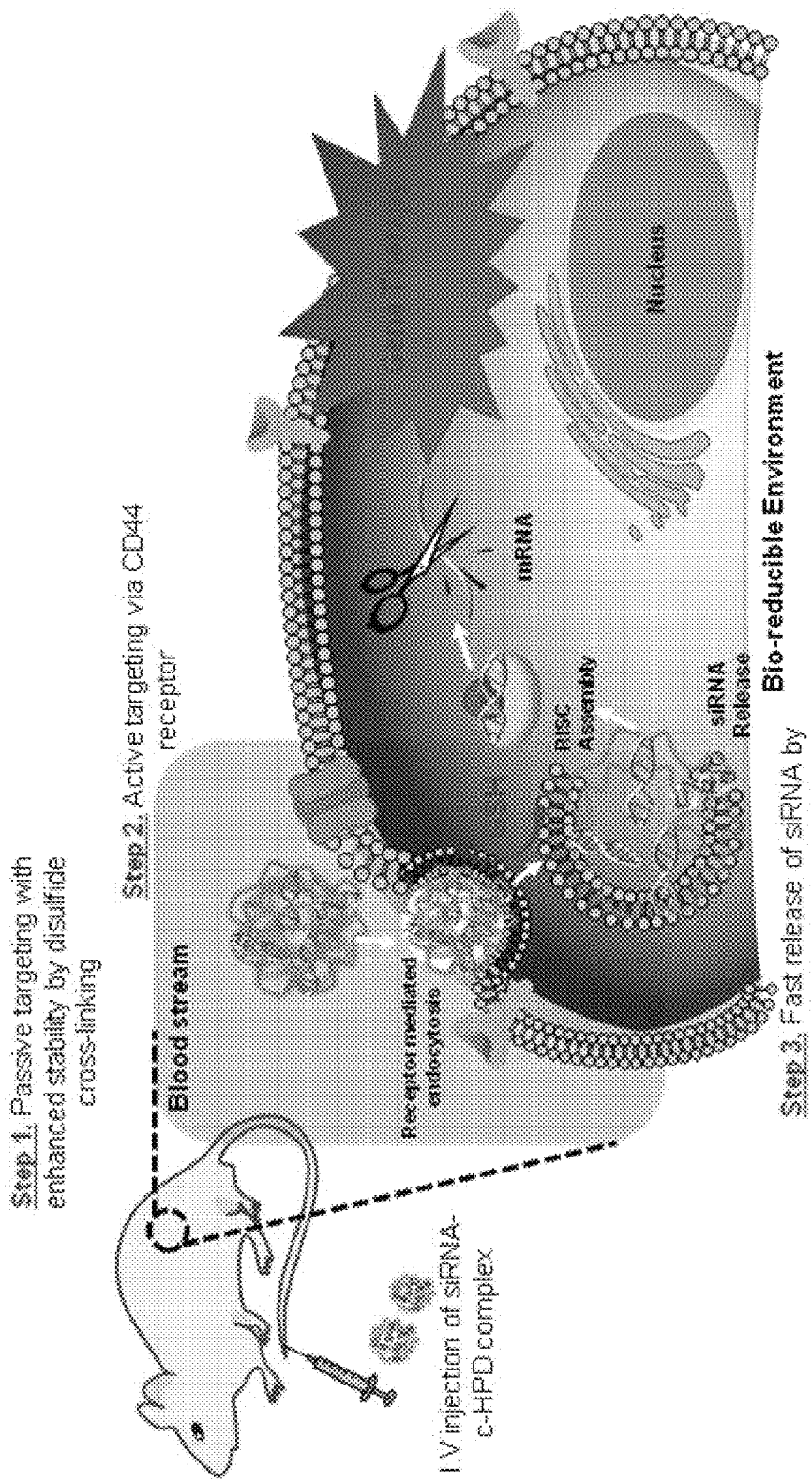
FIG. 1 is a schematic illustrating the gene therapy process in which, after intravenous injection, a siRNA/HA-PDA-P (DMAEMA) complex according to one embodiment is selectively accumulated in a lesion in an animal model.
Figure 2:
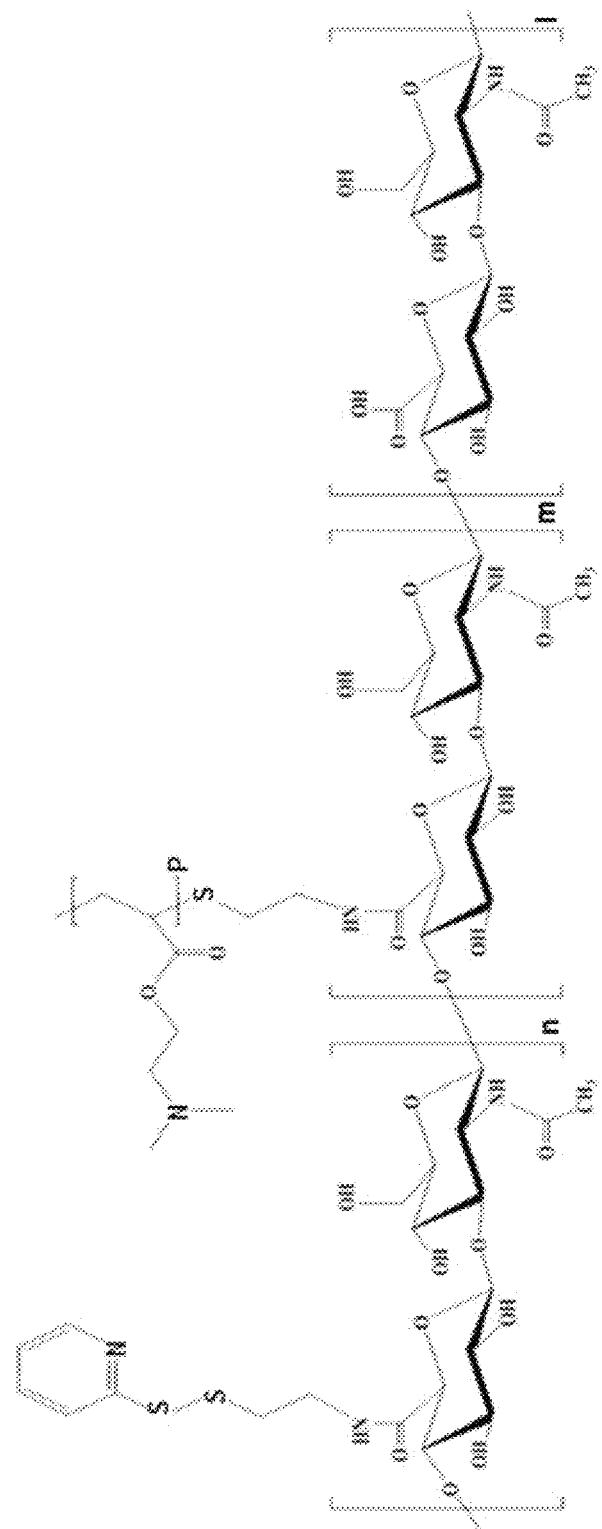
FIG. 2 is a chemical structure of a HA-PDA-P (DMAEMA) conjugate according to one embodiment.

Reference will now be made in detail to embodiments, examples of which are illustrated in the accompanying drawings, wherein like reference numerals refer to like elements throughout. In this regard the present embodiments may have different forms and should not be construed as being limited to the descriptions set forth herein. Accordingly, the embodiments are merely described below, by referring to the figures, to explain aspects of the present description.

Recent reports have disclosed the development of gene or drug delivery systems using disulfide bonds (S—S). Disulfide bonds are involved in reversible redox mechanisms of various biological events. For example, disulfide bonds are readily reduced into thiol groups by glutathione (~10 mM) within cells.

One embodiment of the invention provides a hyaluronic acid conjugate comprising hyaluronic acid, a disulfide bond-containing crosslinking agent, and a cationic, amphiphilic polymer.

Another embodiment provides a hyaluronic acid-nucleic acid complex including the hyaluronic acid conjugate and a nucleic acid in which the hyaluronic acid conjugate is coupled with the nucleic acid.

Another embodiment provides a self-assembling composition (e.g., aggregate or assembly), the composition including a plurality of hyaluronic acid conjugates or a plurality of hyaluronic acid-nucleic acid complexes. For example, the self-assembling composition includes two or more copies of hyaluronic acid conjugates or two or more copies of the hyaluronic acid-nucleic acid complexes, wherein hyaluronic acid conjugates or the hyaluronic acid-nucleic acid complexes are crosslinked to one another.

Another embodiment provides a nucleic acid delivery composition including the hyaluronic acid-nucleic acid complex, the self-assembling composition, or any combination thereof.

Another embodiment provides a method for nucleic acid delivery, the method comprising: administering a hyaluronic acid-nucleic acid complex, the self-assembling composition, or a combination thereof, to a subject in need of the nucleic acid delivery. The method may further include a step of identifying the subject in need of the nucleic acid delivery, before the administering step. The subjects may be mammals including primates such as humans and monkeys and rodents such as mice and rats, or a cell or a tissue which is isolated from a living body or artificially cultured. The administration may be conducted through an oral or parenteral pathway. Parenteral administration may include intravenous injection, subcutaneous injection, muscular injection, intraperitoneal injection, endothelial administration, local administration, intranasal administration, intrapulmonary administration, and rectal administration.

Hyaluronic acid (HA) is an anionic mucopolysaccharide distributed widely throughout the vitreous body, the synovial fluid, the cartilage, and the skin. There is no particular limit in the molecular weights of the hyaluronic acid, and for example, the hyaluronic acid may have weight-average molecular weights ranging from about 1000 Da to about 1,000,000 Da, about 5,000 Da to about 500,000 Da, or about 10,000 Da to about 100,000 Da, when the molecular weight is measured by water-soluble gel permeation chromatography (GPC).

Any compound containing a disulfide bond may be used as a suitable disulfide bond-containing crosslinking agent. In one particular embodiment, the disulfide bond-containing crosslinking agent may comprise pyridyldithioethylamine (PDA), pyridyl disulfide methacrylate (PDSMA), succinimidyl 3-(2-pyridylthio)propionate (SPDP), succinimidyl 6-(3'-[2-pyridyldithio]-propionamido)hexanoate (LC-SPDP), sulfosuccinimidyl 6-(3'-[2-pyridyldithio]-propionamido)hexanoate (sulfo-LC-SPDP), 3,3'-dithiobis(sulfosuccinimidylpropionate (DTSSP) or any combination thereof.

The hyaluronic acid conjugates or the hyaluronic acid-nucleic acid complexes can crosslink to each other (self-assemble) via disulfide bonds, to form an assembly or aggregate (e.g., in a nano-gel from) under reducing conditions (for example, in the presence of a reducing agent).

The crosslinking agent may be chemically bonded to hyaluronic acid by a conventional method (e.g., a catalyst). When the cross linking agent is pyridyldithioethylamine (PDA), for example, its amine group forms a bond with the carboxyl group of hyaluronic acid at a pH of 6 to 7 in the presence of a conventional catalyst.

Depending on the amount of the crosslinking agent, the degree of crosslink bonds in the hyaluronic acid conjugate or the size of nano-gel after crosslinking may vary. For instance, the amount of the crosslinking agent may be such that out of 100 carboxylic acid groups of hyaluronic acid, 1 to 30 carboxylic acid groups react with the crosslinking agent; that is, the amount of the crosslinking agent may be such that the carboxy group of hyaluronic acid is substituted at rate of 1 to 30% with the crosslinking agent.

The cationic, amphiphilic polymer is positively charged in the hydrophobic moiety thereof so that it can be readily associated with a nucleic acid. The amphiphilic polymer refers to a polymer having a polar, water-soluble moiety (hydrophilic moiety) and a nonpolar, water-insoluble moiety (hydrophobic moiety). In addition, the amphiphilicity facilitates the formation of self-assembling compositions or self-aggregates through electrostatic attraction between the polymer and nucleic acid in an aqueous environment (for example, in the case of P(DMAEMA) etc.).

Any cationic, amphiphilic polymer with a weight average molecular weight of $1\times10^2$ Da to $1\times10^5$ Da is suitable for use. In addition, the cationic, amphiphilic polymer may be a biocompatible polymer. In one particular embodiment, the cationic, amphiphilic polymer may comprise poly(dimethylaminoethyl methacrylate) also referred to as P(DMAEMA), chitosan, glycol chitosan, poly-L-lysine, polyethylene imine (PEI), polyamidoamine dendrimer, or any combination thereof. For example, the cationic, amphiphilic polymer may be poly(dimethylaminoethylmethacrylate) with a weight-average molecular weight from about $1\times10^2$ Da to about $1\times10^5$ Da, from about $5\times10^2$ Da to about $1\times10^5$ Da, or from about $1\times10^3$ Da to about $5\times10^4$ Da. The molecular weight of the cationic, amphiphilic polymer may be measured by any conventional method, for example by analyzing a characteristic peak of $^1$H-NMR, but not be limited thereto. Additionally, the molecular weight of a nucleic acid associated with a hyaluronic acid conjugate may be measured by high performance liquid chromatography and/or electrophoresis. Furthermore, the molecular weight of hyaluronic acid conjugates may be measured by dynamic light scattering (DLS), and/or static light scattering (SLS). A conventional scale may be used to measure the ratio of of components within a hyaluronic acid composition. (e.g., the weight ratio of the hyaluronic acid conjugate to nucleic acid associated with said conjugate).

The cationic, amphiphilic polymer may be chemically bonded to hyaluronic acid by a conventional method (e.g., a catalyst). For example, the chemical bond may be formed between the amine group of poly(dimethylaminoethylmethacrylate) and the carboxyl group of hyaluronic acid using a catalyst at a pH of about 6 to about 7.

Depending on the amount of the cationic, amphiphilic polymer present in the conjugate, the size of charge in the hyaluronic acid conjugate may vary. For instance, the amount of the cationic, amphiphilic polymer may be such that, of 100 carboxylic acid groups of hyaluronic acid, 1 to 30 react with the cationic, amphiphilic polymer, that is, such that the carboxyl group of hyaluronic acid is substituted at rate of 1 to 30% with the cationic, amphiphilic polymer.

In one embodiment, the hyaluronic acid conjugate may have the structure of Chemical Formula 1 (wherein l, m, and n are respectively numbers of hyaluronic acid units (each inclusive of one carboxyl group), wherein n is the number of hyaluronic acid units linked with a crosslinking agent, accounting for 1 to 30% of l+m+n, and m is the number of hyaluronic acid units linked with a cationic and amphiphilic polymer, accounting for 1 to 30% of l+m+n, the units of n, m and l may be positioned in any order, l+m+n being an integer of about 2 to about 20,000, particularly about 2 to about 10,000, about 2 to about 5000, or about 2000 to about 2500 (corresponding to a molecular weight of about 1000 Da to about 10,000,000 Da, about 1,000 Da to about 5,000,000 Da, about 1000 Da to about 2,500,000 Da, or about 800,000 Da to about 1,200,000 Da).

[Chemical Formula 1]

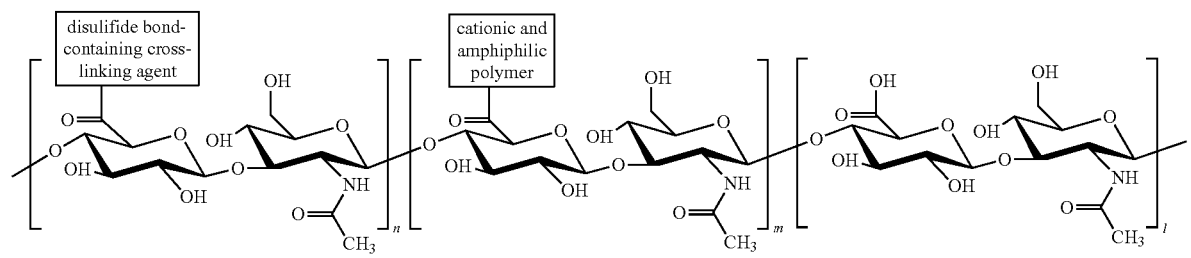

In another embodiment, a hyaluronic acid conjugate having pyridyldithioethylamine as a disulfide bond-containing linking agent and poly(dimethylaminoethylmethacrylate) as a cationic, amphiphilic polymer may be represented by the following Chemical Formula 2 (wherein l, m, and n are as defined

[Chemical Formula 2]

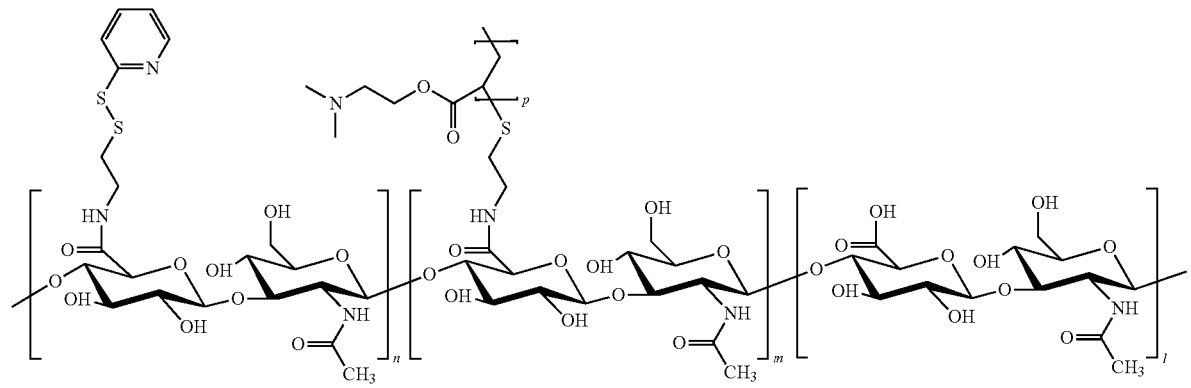

The hyaluronic acid conjugate is capable of interacting with a nucleic acid to form a hyaluronic acid-nucleic acid complex via electrostatic attraction between the nucleic acid and the cationic, amphiphilic polymer of the conjugate.

Suitable nucleic acids may comprise any single- or double-stranded nucleic acid including deoxyribonucleic acid (DNA), ribonucleic acid (RNA), and polynucleotide derivatives in which the backbone, the sugar, or the base is chemically modified or which is modified at the terminus thereof. In detail, the nucleic acid may be selected from the group consisting of RNA, DNA, siRNA (short interfering RNA), an aptamer, antisense ODN (oligodeoxynucleotide), antisense RNA, ribozyme, DNAzyme, or any combination thereof. For example, the nucleic acid may be suitable for gene therapy and may include an siRNA (short interfering RNA), an aptamer, an antisense oligodeoxynucleotide, and an antisense RNA, with preference for siRNA.

In the hyaluronic acid-nucleic acid complex, the amount of the nucleic acid present can be adjusted along with the amount of the cationic, amphiphilic polymer. The complex may comprise the hyaluronic acid conjugate and the nucleic acid at a weight ratio from about 99:1 to about 5:95 (weight of hyaluronic acid : weight of nucleic acid). In an embodiment, the ratio of hyaluronic acid conjugate to nucleic acid is from about 2:1 to about 30:1, or from about 5:1 to about 25:1.

Figure 10:
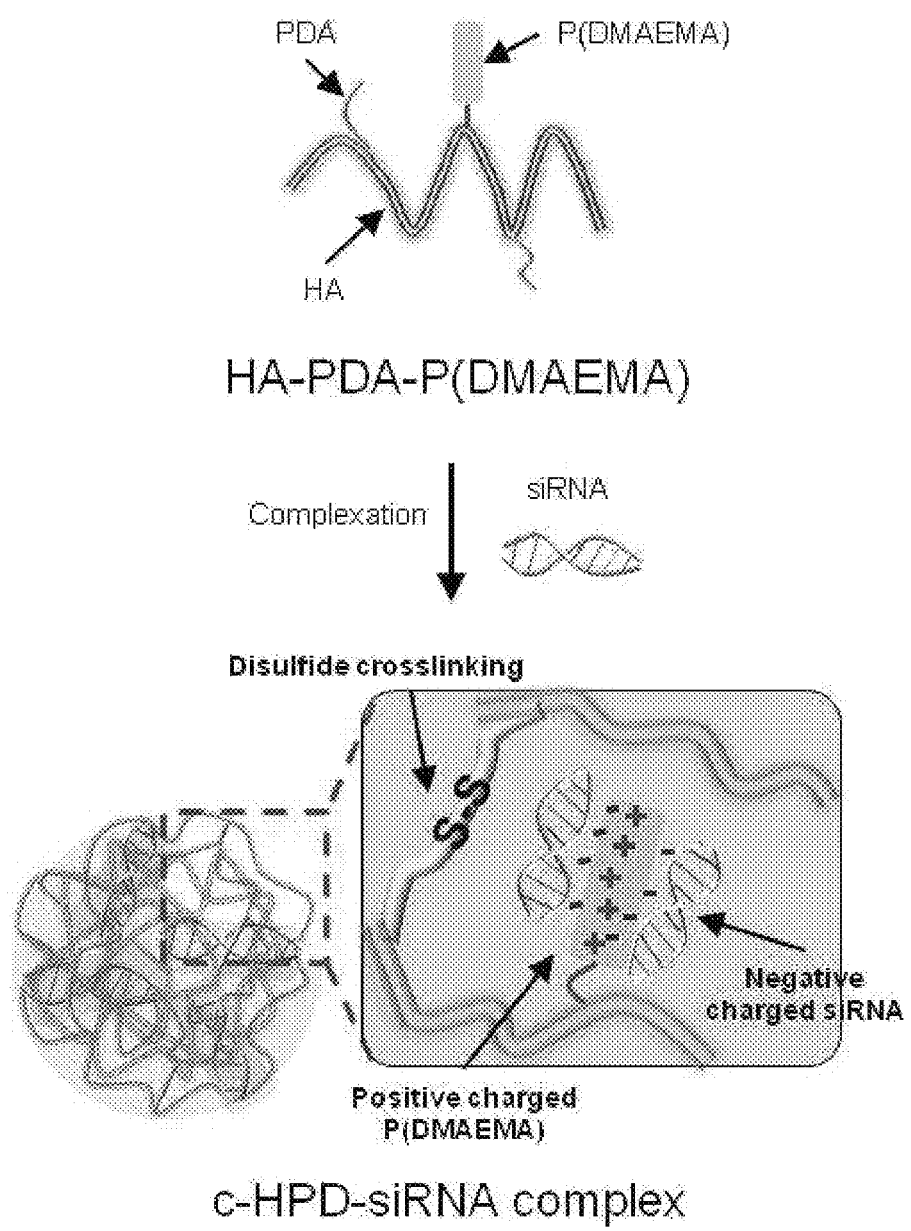
FIG. 10 is a schematic illustrating a process in which the hyaluronic acid-nucleic acid complex according to according to an embodiment is self-assembled.

Through the crosslinking agent, hyaluronic acid conjugates or hyaluronic acid-nucleic acid complexes may be crosslinked with one another to form a self-assembling composition with the hydrophilic regions in contact with a surrounding solvent, sequestering the hydrophobic region, whether combined with the nucleic acid or not, in the composition center (See FIG. 10). The self-assembly of the hyaluronic acid conjugate or the hyaluronic acid-nucleic acid complex may range in average diameter from about 1 nm to about 2000 nm, or from about 10 nm to about 800 nm.

The cross linkage of the self-assembling composition may be formed by treating a plurality of the hyaluronic acid conjugates with a reducing agent. This reducing agent may comprise dithiothreitol (DTT), glutathione, 2-thiazoline-2-thiol, 2-propen-1-tiol, or any combination thereof As the crosslinkage is formed among the hyaluronic acid conjugates or among the hyaluronic acid-nucleic acid complexes, both the targeting ability and cumulativity of the conjugates and/or complexes may be improved (See FIGS. 11 and 12).

Another embodiment provides a self-assembling composition including hyaluronic acid-nucleic acid complexes according to an embodiment, wherein the hyaluronic acid-nucleic acid complexes are crosslinked to one another.

The nucleic acid may be designed for use in gene therapy, and may be siRNA available for the treatment of one or more pulmonary diseases (e.g., RSV, Flu, SARS, influenza, etc.), ophthalmic diseases (e.g., AMD, etc.), neurological diseases (e.g., depression, Alzheimer's, Huntington's disease, spinocoerebral ataxia, ALS, neuropathic pain, encephalitis, etc.), cancer (e.g., glioblastoma, human papillomavirus, prostate, adenocarcinoma, etc.), digestive diseases (e.g., irritable bowel disease), hepatic diseases (e.g., HBV, hypercholesterolemia, etc.), autoimmune diseases (e.g., rheumatoid arthritis, etc.), articular pathology (e.g., rheumatoid arthritis), venereal diseases (e.g., HSV), or any combination thereof. Accordingly, the hyaluronic acid-nucleic acid complex may be applied to the prevention and/or treatment of the above-mentioned diseases.

Hyaluronic acid-nucleic acid complexes according to an embodiment may crosslink via intermolecular disulfide bonds to form a nano-sized self-assembling composition or self-aggregate, and can be selectively accumulated within target cells. The hyaluronic acid enables the hyaluronic acid-nucleic acid complex to be used for disease targeting because it is capable of specifically binding CD44 receptors overexpressed on the surface of cancer cells.

Another embodiment provides a method for preparing the hyaluronic acid conjugate or the hyaluronic acid-nucleic acid complex.

The method for preparing the hyaluronic acid conjugate comprises the steps of:

(1) reacting a hyaluronic acid with a disulfide bond-containing, cationic, amphiphilic polymer; and (2) reacting the cationic, amphiphilic polymer-bound hyaluronic acid with a crosslinking agent.

In this method, steps (1) and (2) may be performed in any order.

In one embodiment, the method for preparing the hyaluronic acid-nucleic acid complex comprises the steps of:

(1') reacting a hyaluronic acid with a disulfide bond-containing, cationic, amphiphilic polymer;

(2') reacting the cationic, amphiphilic polymer-bound hyaluronic acid with a crosslinking agent; and (3) associating the resulting modified hyaluronic acid with a nucleic acid.

In this method, the order of steps (1') and (2') may be performed in any order, and step (3) is performed after steps (1) and (2).

The method for preparing a hyaluronic acid-nucleic acid complex may further include the step of: (4) treatment with a reducing agent after step (3). After treatment with a reducing agent, the hyaluronic acid-nucleic acid complexes can crosslink via disulfide bonds. The reducing agent available for the crosslinkage may comprise dithiothreitol (DTT), glutathione, 2-thiazoline-2-thiol, 2-propene-1-tiol, or any combination thereof.

The components used in the method are as described above. In addition to exhibiting significantly improved in in vivo stability due to the disulfide bridge, the hyaluronic acid conjugate or the hyaluronic acid-nucleic acid complex can effectively deliver a nucleic acid to an affected region with the help of hyaluronic acid's ability to target diseased cells without exerting toxicity on normal cells (See FIG. 4), and shows high delivery efficiency of nucleic acids (See FIGS. 6 and 7), thus eliciting a maximum effect of gene therapy with nucleic acids (See FIG. 8), with minimal side effects. Thus, if the therapeutic effects of the conjugate or the complex are identified in models of various diseases, they can be useful as therapeutics for a wide spectrum of diseases.

The novel siRNA delivery system, which may be in the form of a HA-PDA-P(DMAMEA) siRNA complex, has an advantage over conventional amphiphilic siRNA delivery systems in that it exhibits less non-specific cytotoxicity. Further, the novel siRNA delivery system may form a nano-sized aggregate, thus taking advantage of the EPR characteristics of cancer cells, and exhibits higher selectivity for diseases of interest (e.g., cancer) because of HA's ability to specifically bind to receptors of cancer cells. Thus, the present invention allows a greater amount of siRNA to accumulate within cancer cells, exerting significant therapeutic activity. Moreover, the embodiments of the invention crosslinked via disulfide bridges, has high stability in vivo, and constantly releases the drug over a long period of time with sufficient selectivity for target cells, without exerting cytotoxicity on normal cells. Therefore, the siRNA delivery system can be used in research into the treatment of intractable diseases such as cancer.

Hereafter, the invention will be described in detail by examples.

The following examples are intended merely to illustrate the invention and are not construed to restrict the invention.

EXAMPLES

Example 1

Synthesis of Poly(Dimethylaminoethyl Methacrylate) (P(DMAEMA))

Figure 3:
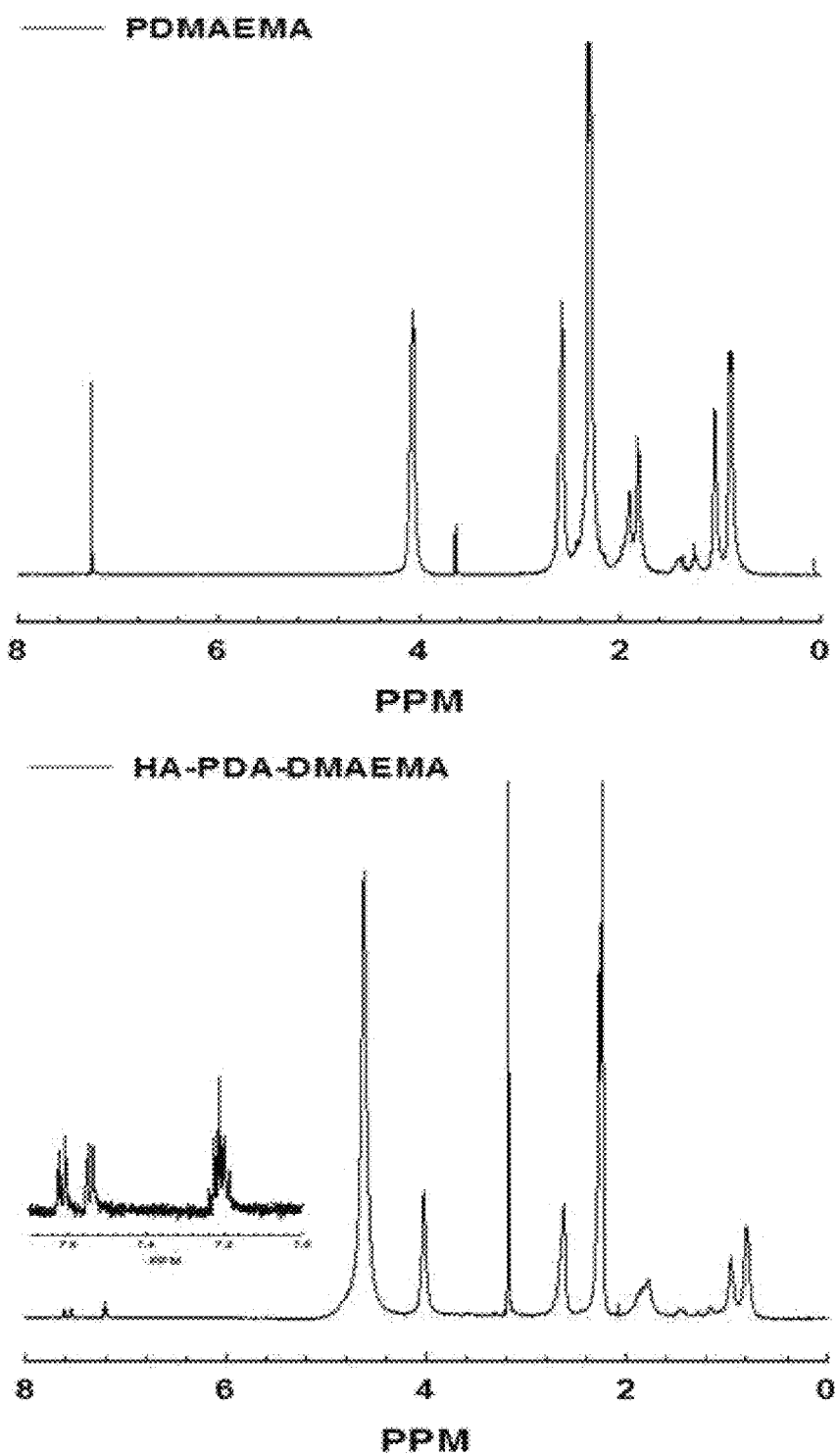
FIG. 3 is a graph showing 1H-NMR spectra of P(DMAEMA) (upper) and a HA-PDA-P(DMAEMA) conjugate (lower).

In 10 ml of methanol were dissolved 3.22 ml of DMAEMA, 72.28 mg of AESH-HCl (2-aminoethanethiol hydrochloride) and 31.4 mg of AIBN (azobisisobutyronitrile), followed by repeating a freeze-thaw process three times to remove oxygen from the reactor. A reaction was then conducted at 70° C. for 6 hrs while stirring. After completion of the reaction, the reaction mixture was dialyzed against water/methanol (1:1 v/v) through a semipermeable membrane with an MWCO (Molecular Weight Cut Off) of 1000 Da to remove the catalyst and unreacted materials, and lyophilized to yield P(DMAEMA) as a white powder. The NMR spectrum of P(DMAEMA) is given in FIG. 3 (upper panel). Based on the NMR spectrum of FIG. 3, the polymer was structurally identified using the characteristic peaks at 2.2-2.4 ppm, 2.5 ppm, 3.6 ppm, and 4 ppm, and was found to have a molecular weight of 8000 Da as calculated from area ratios of the characteristic peaks. The total yield was 85% or higher.

The reaction is illustrated in Reaction Scheme 1, below.

[Reaction Scheme 1]

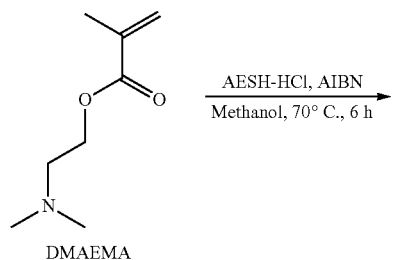

DMAEMA

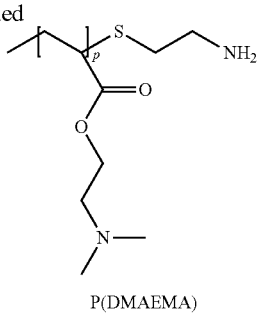

P(DMAEMA)

(wherein, the molecular weight of DMAEMA monomer is 157.2 g/mol, the molecular weight of the prepared PDMAEMA is 8 KDa, and p (repeating number) is 51)

Example 2

Preparation of Hyaluronic acid (HA)-Pyridyldithioethylamine (PDA) Conjugate

To introduce a functional group able to form a disulfide bond therein, HA was reacted with pyridyldithioethylamine (PDA) in the presence of the catalysts EDC (1-ethyl-3-(3-dimethylaminopropyl)carbodiimide) and HOBt (hydroxybenzotriazole).

First, 100 mg of HA with a molecular weight of 67 KDa and 60.58 mg of EDC were dissolved in 25 ml of deionized water to form an HA solution. A solution of 17.54 mg of PDA-HCl and 42.7 mg of HOBt in 25 ml of methanol was slowly added, dropwise, to the HA solution. The resulting solution was adjusted to pH 6.6-6.8, and PDA was introduced into HA at room temperature for 24 hrs while stirring. After completion of the reaction, the reaction mixture was dialyzed against water/ethanol (1:1 v/v) through a semipermeable membrane with an MWCO of 12~14 KDa to remove the catalysts and unreacted materials. Lyophilization of the dialysate afforded an HA-PDA conjugate as a white powder. The total yield was 87% or higher. The HA-PDA was found to have 6.7 PDA molecules per 100 HA units as measured by spectrometry (UV-Vis absorbance 343 nm) for pyridine-2-thione released from PDA after treatment with DTT (degree of substitution: 6.7%). From the results, the HA-PDA was calculated to have an average molecular weight of 68.9 KDa These reactions are given as illustrated in Reaction Scheme 2.

[Reaction Scheme 2]

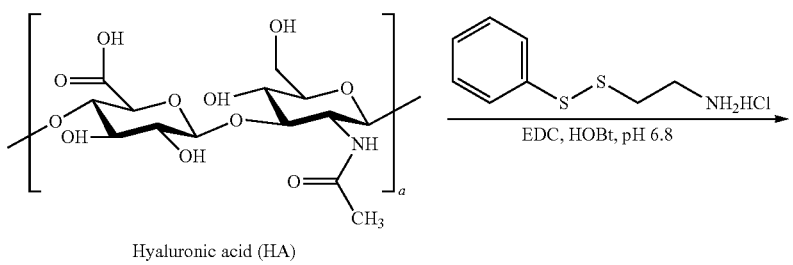

Hyaluronic acid (HA)

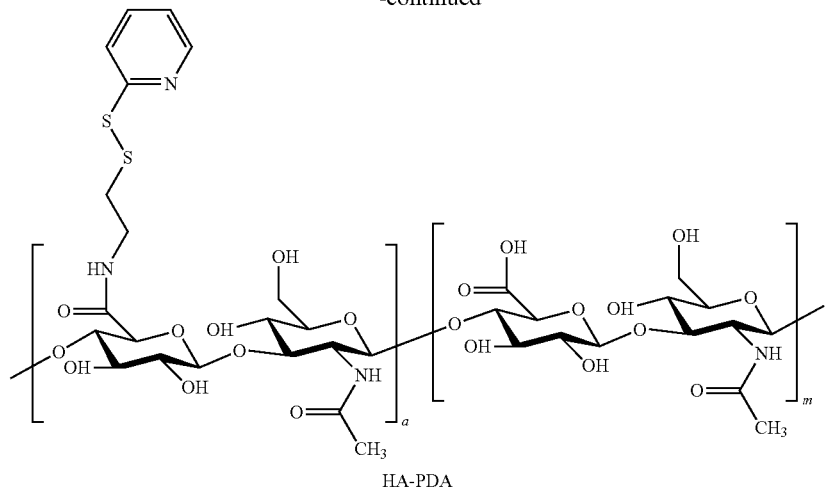

HA-PDA (wherein the molecular weight of the repeat unit of HA is 410 Da, and thus, when the molecular weight of HA is 67 KDa HA, a is 163;

n is 11, since the substitution ratio of PDA is 6.7% (e.g., the number of PDA per 100 units of HA is 6.7; and m is 152, since it refers to the number of repeat units other than a and n).

Example 3

Preparation of HA-PDA-P(DMAEMA) Conjugate

To introduce a positively charged functional group therein, the HA-PDA conjugate was reacted with P(DMAEMA) in the presence of the catalysts EDC (1-ethyl-3-(3-dimethylaminopropyl)carbodiimide) and HOBt (hydroxybenzotriazole).

100 mg of the HA-PDA prepared in Example 2 and 20.16 mg of EDC were dissolved in 25 ml of deionized water to form an HA-PDA solution. A solution of 213.54 mg of the P(DMAEMA) prepared in Example 1 and 14.25 mg of HOBt in 25 ml of methanol was slowly added, dropwise, to the HA-PDA solution. The resulting solution was adjusted to pH 6.6-6.8, and P(DMAEMA) was introduced into HA at room temperature for 24 hrs while stirring. After completion of the reaction, the reaction mixture was dialyzed against water/ethanol (1:1 v/v) through a semi-permeable membrane with an MWCO of 12~14 KDa to remove the catalysts and unreacted materials. Lyophilization of the dialysate yielded an HA-PDA-P(DMAEMA) conjugate as a white powder. The total yield was 90% or higher. The HA-PDA-P(DMAEMA) was found to have 6.7 PDA molecules (6.7%) and 2 P(DAEMA) molecules (2.0%) per 100 HA units. The HA-PDA was calculated to have an average molecular weight of 97.4 KDa.

This reaction is given as illustrated in Reaction Scheme 3.

[Reaction Scheme 3]

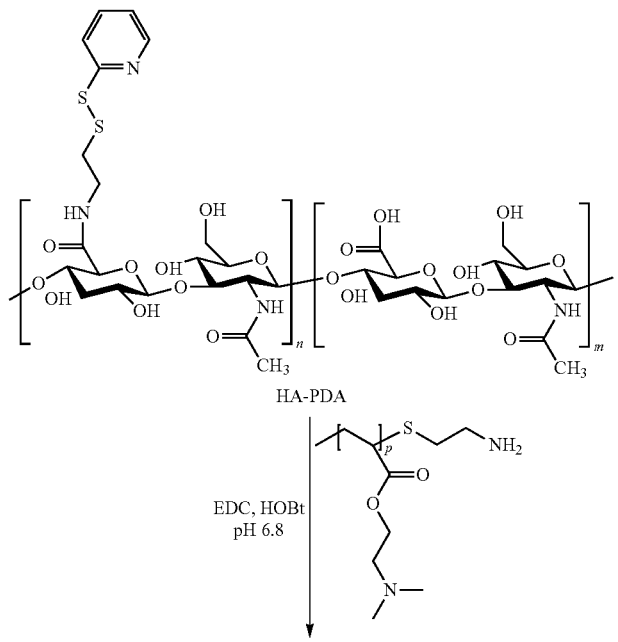

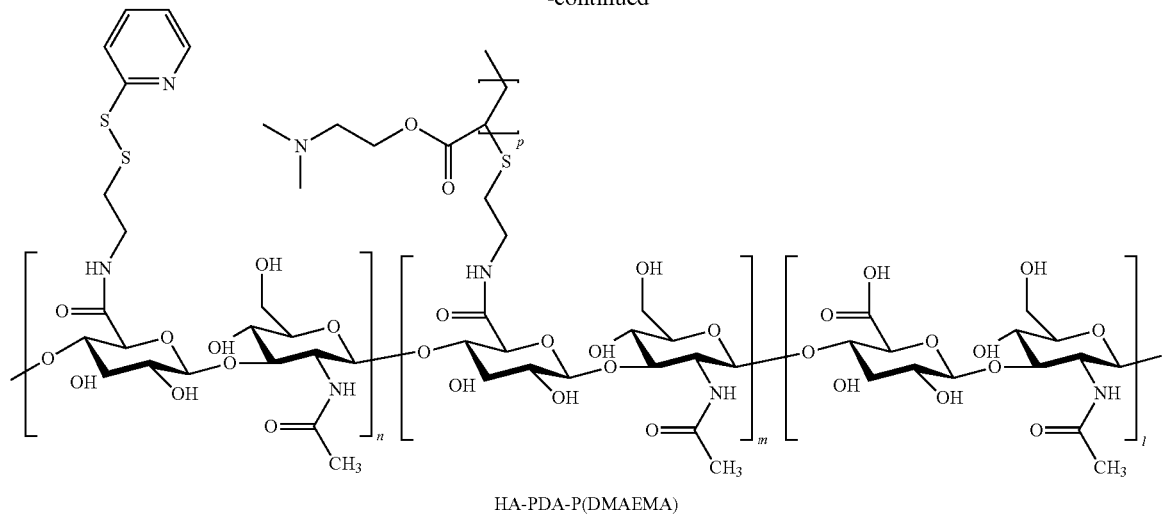

HA-PDA-P(DMAEMA)

(wherein n is 11, m is 4, and l is 148)

Example 4

Analysis of Chemical Properties of HA-PDA-P(DMAEMA) Conjugate

An analysis was made of the molecular weight of the P(DMAEMA) prepared in Example 1 and the degrees of substitution of PDA and P(DMAEMA) in the HA-PDA-P(DMAEMA) conjugate prepared in Example 3. To perform this analysis, each compound was dissolved at a concentration of 5 mg/ml in $CD_3OD/D_2O$ (1:1 v/v), and analyzed for structural features of P(DMAEMA) (upper panel in FIG. 3) and the HA-PDA-P(DMAEMA) conjugate (lower panel in FIG. 3) using 500 MHz $^1$H-NMR. The results are given in FIG. 3. As can be seen in the lower panel of FIG. 3, the HA-PDA-P(DMAEMA) conjugate had a degree of substitution of 6.7% for PDA and 4.5% for P(DMAEMA).

Example 5

Assay for Cytotoxicity of HA-PDA-P(DMAEMA) Conjugate

The HA-PDA-P(DMAEMA) conjugate prepared in Example 3 was assayed for cytotoxicity in the melanoma cell line B16F10 and the fibroblast cell line NIH3T3.

In further detail, B16F10 cells (American Type Culture Collection (ATCC), USA) or NIH3T3 cells (American Type Culture Collection (ATCC), USA) were seeded at a density of $5\times10^3$ cells into 96-well plates, and stably maintained at 37° C. for 24 hrs in an RPMI1640 medium (supplemented with FBS 10% (v/v) and AA 1% (v/v); Welgene, Korea). Then, the cells were incubated with 10 or 100 μg/ml of the HA-PDA-P(DMAEMA) conjugate prepared in Example 3 in an Opti-MEM medium (Gibco, USA) for 12 hrs at 37° C. in a 5% $CO_2$ incubator. Subsequently, an MTT (3-(4,5-dimethylthiazol-2-yl)-2,5-diphenyltetrazolium bromide) solution (5 mg/ml, dissolved in DPBS) was added to an amount of 10 volume % of the RPMI 1640 medium to each well, followed by incubation at 37° C. for an additional 1 hr. The formazan crystals that were subsequently formed were dissolved in DMSO (dimethyl sulfoxide) before absorbance at 570 nm was read on a microplate reader to determine cell viability.

Figure 4:
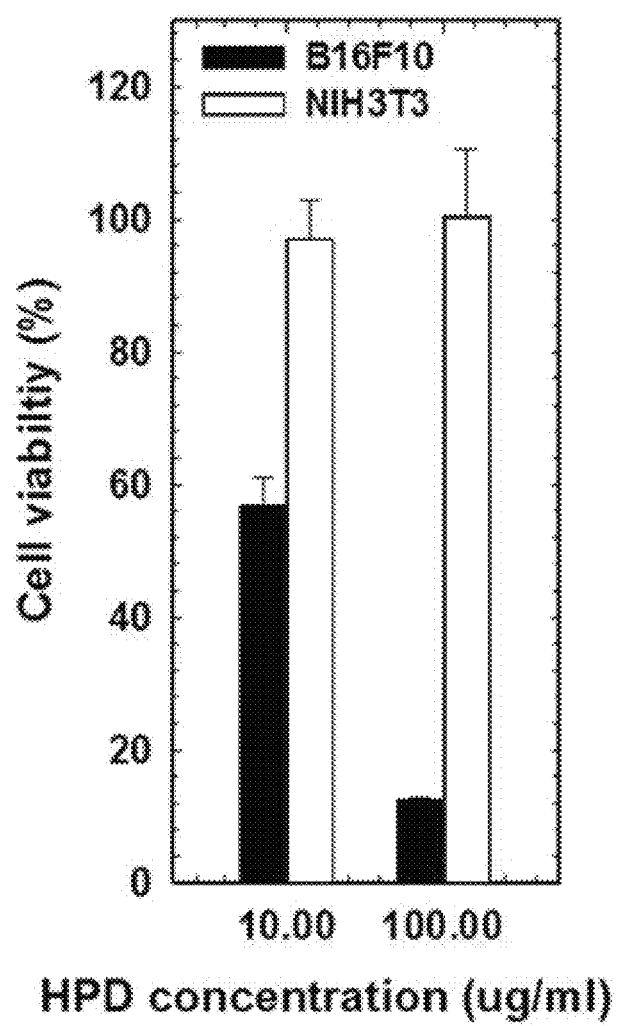
FIG. 4 is a graph of cell viability plotted against concentration showing the cytotoxicity of a HA-PDA-P (DMAEMA) conjugate against B16F10 (melanoma cells, filled bar, left) and NIH3T3 (fibroblast cells, empty bar, right) measured in terms of cell viability after exposure to various concentrations of the HA-PDA-P(DMAEMA) conjugate.

The results are given in FIG. 4. As shown in FIG. 4, the HA-PDA-P(DMAEMA) conjugate exerts almost no toxicity on the normal cell line NIH3T3, but is highly toxic to the cancer cell line B16F10. This selectivity is believed to be attributed to the fact that the HA-PDA-P(DMAEMA) conjugate has high cell permeability due to the CD44 receptor on the surface of cancer cells.

Example 6

Assay for siRNA/HA-PDA-P(DMAEMA) Complex Formation Behavior

To evaluate the complex formation behavior between the HA-PDA-P(DMAEMA) conjugate prepared in Example 3 and siRNA, electrophoresis was performed on 8% (w/v) acrylamide gel.

In further detail, 5 mg of the HA-PDA-P(DMAEMA) conjugate prepared in Example 3 was dissolved in 1 ml of DEPC (diethyl pyrocarbonate)-treated PBS (pH 5.0, 150 mM NaCl) to give a stock solution. The siRNA used in this experiment comprised siRFP composed of a sense strand 5'-UGU AGA UGG ACU UGA ACU CdTdT-3' (SEQ ID NO: 1-dTdT) and an antisense strand 5'-GAG UUC AAG UCC AUC UAC AdTdT-3 ' (SEQ ID NO: 2-dTdT), siRFP was dissolved at a concentration of 1 mg/ml in 1 ml of DEPC-treated PBS (pH 7.4, 150 mM NaCl) to generate a stock solution. The term "siRNA" used in the following Examples refers to the siRFP.

To analyze the formation behavior of the complex depending on the amount of the HA-PDA-P(DMAEMA) conjugate, 1 μg, 5 μg, 10 μg, or 20 μg of the HA-PDA-P(DMAEMA) conjugate was mixed with 1 μg of siRFP, and incubated at 37° C. for 1 hr to form a complex. Thereafter, the complex was sufficiently mixed with 1 μl of 15 μM DTT at 37° C. for 20 min to form crosslinkages.

Figure 5:
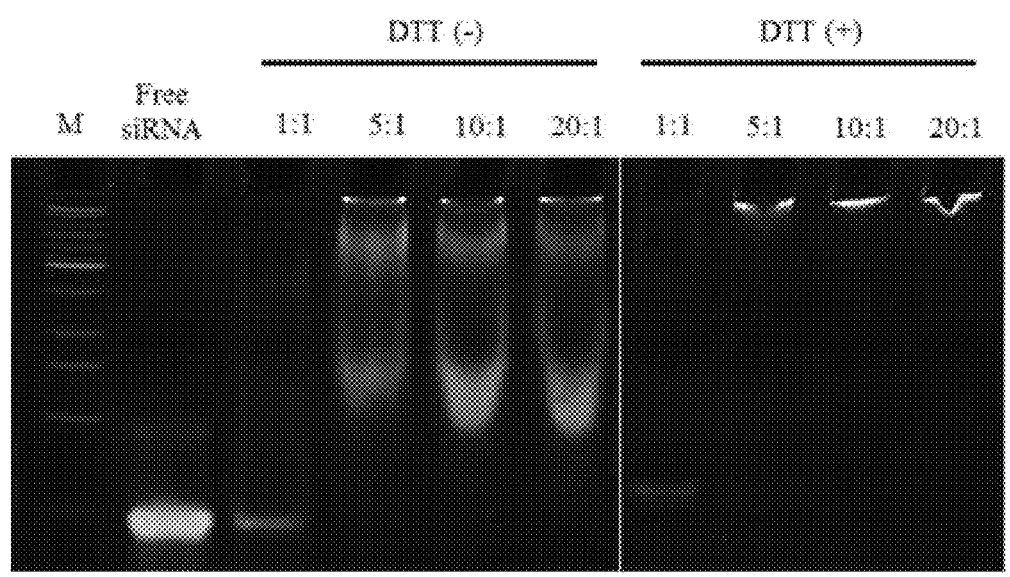
FIG. 5 depicts a gel electrophoresis showing the formation behavior of a siRFP/HA-PDA-P(DMAEMA) complex according to the weight ratio of siRFP to the HA-PDA-P (DMAEMA) conjugate, and the formation behavior of the complex after treatment with DTT, as analyzed by electrophoresis.

The complex was identified by electrophoresis. In this regard, the reaction mixtures were run on an 8% (w/v) acrylamide gel in the presence of an electric field, followed by visualizing siRFP bands. The results are given in FIG. 5. As is understood from the data of FIG. 5, when various weight ratios of the HA-PDA-P(DMAEMA) conjugate to siRNA ranging from 1:1 to 20:1 were used, the formation of the complex started from the weight ratio of 5:1 (5:1, 10:1, 20:1). In the absence of a reducing agent (DTT), bands of the complexes, although positioned higher than free siRNA, were observed to be partially dragged downwards, indicating that they were not compactly formed. There were no dragged bands for complexes exposed to the reducing agent, indicating that the complexes were compactly formed in the presence of the reducing agent because they were crosslinked with one another. These data reveal that the complex is preferably formed from a weight ratio of at least 5:1 between the HA-PDA-P(DMAEMA) conjugate and siRNA in the presence of a reducing agent.

Example 7

Assay for siRNA Stability in siRNA/HA-PDA-P(DMAEMA) Complex

The siRFP/HA-PDA-P(DMAEMA) complex prepared in Example 6 (HA-PDA-P(DMAEMA) (conjugate:siRNA (siRFP)=20:1 w/w) was analyzed for siRFP stability at various intervals in 50% (v/v) mouse serum. To evaluate the stability of siRFP with time, with reference to Example 6, 20 μg of the HA-PDA-P(DMAEMA) conjugate was reacted with 1 μg of siRFP at 37° C. for 1 hr, followed by treatment with 1 μl of 1 M DTT and 40 μg of heparin. Electrophoresis was performed on 8% (v/v) acrylamide gel to detect siRFP bands at 0, 1, 3, 6, 9 and 24 hrs.

Figure 9:
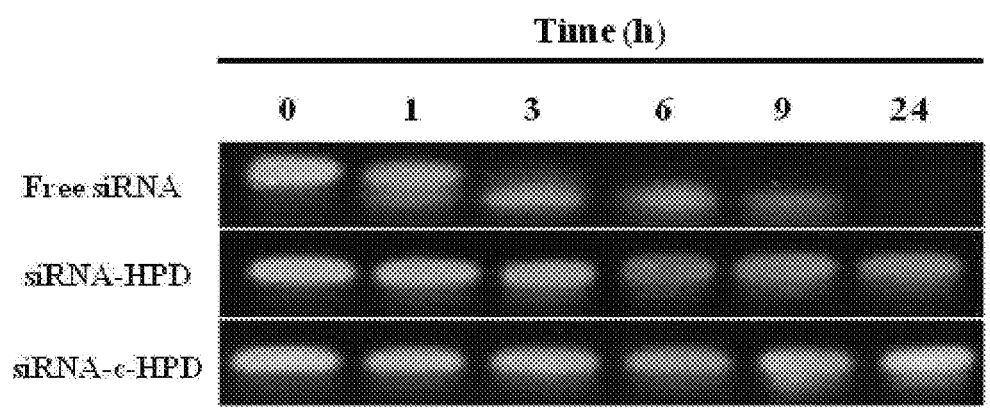
FIG. 9 is a photograph of an acrylamide gel on which a siRFP/HA-PDA-P(DMAEMA) complex according to an embodiment, and free siRNA were run after heparinization, which shows the stability of siRNA (siRFP) in the complex.

The results are shown in FIG. 9. In FIG. 9, siRNA-HPD is a complex of the HA-PDA-P(DMAEMA) conjugate with siRNA (siRFP), formed in the absence of a reducing agent (DTT) (not crosslinked), while c-siRNA-HPD denotes a complex of the HA-PDA-P(DMAEMA) conjugate with siRNA (siRFP) formed via disulfide bridges in the presence of a reducing agent. As can be seen in FIG. 9, siRFP bands of free siRNA degraded with time, whereas siRFP bands that were a part of complexes were maintained with time. In particular, the complexes, when crosslinked, allowed the siRFP bands to remain more intact. These data demonstrate that the complex increases the stability of siRNA.

Example 8

Assay for Cell Permeability Behavior of siRNA/HA-PDA-P(DMAEMA) Complex

To evaluate cell permeability behavior, an siRFP/HA-PDA-P(DMAEMA) complex was prepared in the same manner as in Example 6, with the exception that siRFP labeled with FITC (fluorescein isothiocyanate) was used instead of bare siRFP (HA-PDA-P(DMAEMA) (conjugate:siRNA (siRFP)=20:1 w/w). B16F10 cells (ATCC) and NIH3T3 cells (ATCC) were seeded at a density of $5\times10^3$ cells/well into respective 8-well chamber slides and stabilized for 24 hrs. The cells were treated for 30 min with the siRFP/HA-PDA-P(DMAEMA) complex in such an amount that siRFP was present at a concentration of 50 nM. For comparison of siRNA delivery efficiency, non-treated cells (control) and cells treated with 50 nM free siRFP were used.

The cells were washed twice with DPBS (Dulbecco's Phosphate Buffered Saline) and fixed in a fixation buffer (DPBS containing 4 volume % of para-formaldehyde). After completion of the fixation, the cells were treated with a DAPI (4′,6-diamidino-2-phenylindole) fluorophore-containing mount buffer (DAPI Fluoromount G solution, Southern-Biotech, USA) to stain the nuclei, followed by observing fluorescent images by fluorescence microscopy.

Figure 6:
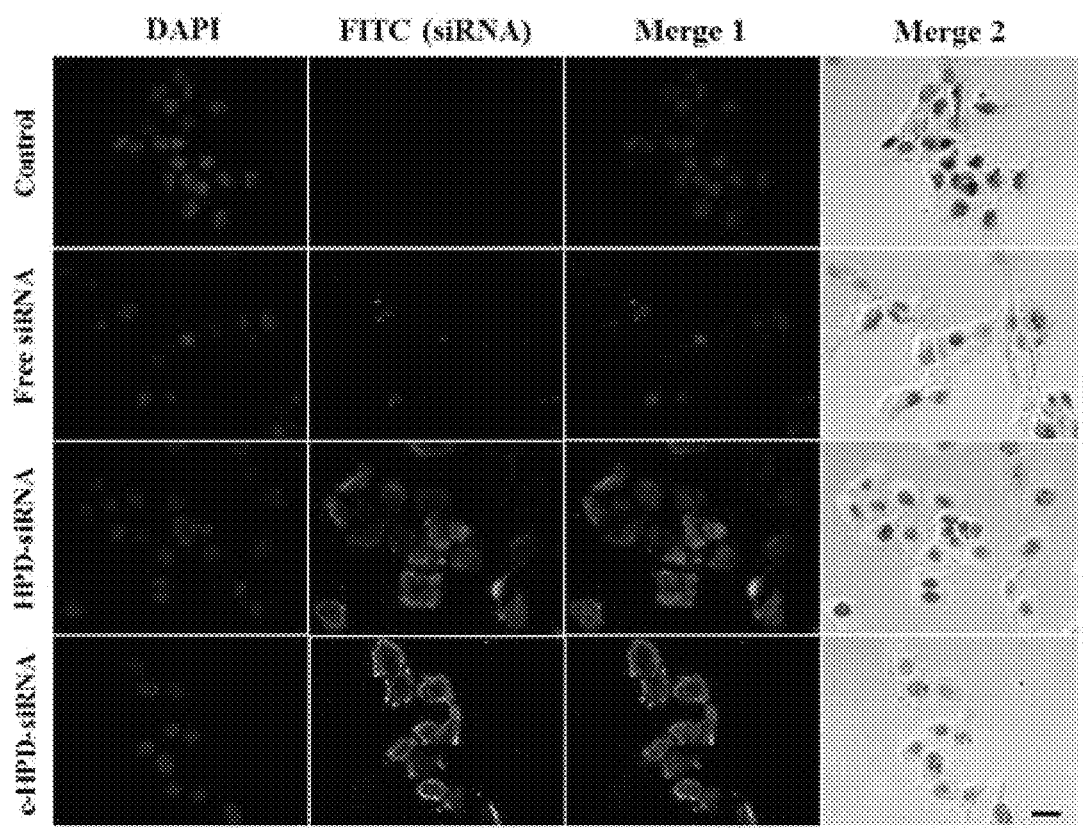
FIG. 6 displays fluorescent images showing the cellular uptake behavior of a FITC-labeled siRFP/HA-PDA-P (DMAEMA) complex in B16F10 cells, as analyzed by fluorescence microscopy (scale bar: 25 μm).
Figure 7:
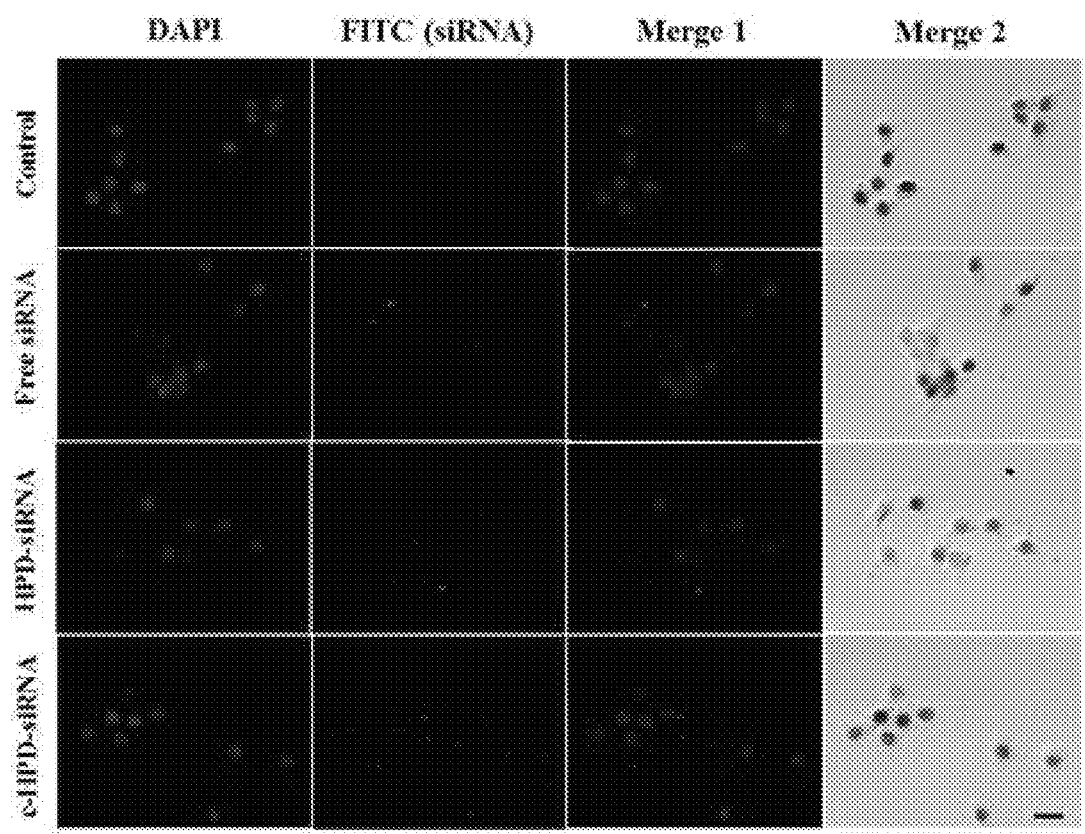
FIG. 7 displays fluorescent images showing the cellular uptake behavior of the FITC-labeled siRFP/HA-PDA-P (DMAEMA) complex in NIH3T3 cells, as analyzed by fluorescence microscopy (scale bar: 25 μm).

The results are shown in FIGS. 6 (B16F10 cells) and 7 (NIH3T3 cells). In FIGS. 6 and 7, siRNA-HPD represents a complex of the HA-PDA-P(DMAEMA) conjugate with siRNA (siRFP), formed in the absence of a reducing agent (DTT) (not crosslinked), while c-siRNA-HPD refers to a complex of the HA-PDA-P(DMAEMA) conjugate with siRNA (siRFP), formed via disulfide bridges in the presence of a reducing agent.

As can be seen in FIG. 6, weak fluorescence was detected from the cytoplasm of cancer cells when they were treated with free siRFP whereas a high fluorescent intensity was observed when they are treated with the siRFP/HA-PDA-P(DMAEMA) complex, indicating that the FITC-labeled siRFP/HA-PDA-P(DMAEMA) penetrated into the cytoplasm of the cancer cells. In contrast, as shown in the fluorescence images of FIG. 6, neither free siRFP nor the free siRFP/HA-PDA-P(DMAEMA) complex was permeable to normal cells. Results of FIGS. 6 and 7 demonstrate that the siRFP(siRNA)/HA-PDA-P(DMAEMA) complex according to a particular embodiment can deliver siRNA into cancer cells within a short time by specific interaction between the HA of the complex and the CD44 receptor overexpressed on cancer cell surfaces, with a significant reduction in the side effect caused by non-specific penetration into normal cells such as NIH3T3.

Example 9

Assay for Gene Therapy Efficacy of siRNA/HA-PDA-P(DMAEMA) Complex

The gene therapy efficacy of the siRFP/HA-PDA-P(DMAEMA) complex was evaluated in terms of siRNA delivery efficiency in RFP-B16F10 cells using fluorescence microscopy.

In further detail, RFP-B16F10 cells expressing the RFP (red fluorescence protein) were seeded at a density of $5\times10^3$ cells/well into 8-well chamber slides and stabilized for 24 hrs. RFP-B16F10 cells (red fluorescence protein (RFP)-expressing B10F10 cells) were prepared as follows (see *Clin Cancer Res* 2008;14:2841-2849). pDSRed2 (1 μg) and Lipofectamine (1 μg, Invitrogen) were mixed in 100 μl of Opti-MEM (Gibco, USA) at room temperature for 10 min and at 37° C. for an additional 20 min. B16F10 cells (ATCC, USA; $1\times10^6$ cells) were incubated with 100 μl of the resulting pDSRed2/Lipofectamine mixture for 4 hrs at 37° C. in a 5% $CO_2$ atmosphere. Thereafter, the medium was exchanged with RPMI 1640, followed by incubation at 37° C. for an additional 2 days in a 5% $CO_2$ atmosphere (transfection efficiency: 30~40%). To separate RFP-expressing cells, the cells were cultured by 2-15 passages in an RPMI 1640 medium containing G418 (1 mg/ml, Life Technologies, USA).

After the cells were treated for 30 min with the siRFP/HA-PDA-P(DMAEMA) complex (HA-PDA-P(DMAEMA) conjugate:siRFP=20:1) of Example 6 in such an amount that siRFP was present at a concentration of 50 nM. The medium was then aspirated. Then, the cells were washed twice with DPBS to remove the matter which remained unabsorbed into the cells, and were incubated for 24 hrs.

To compare the therapeutic efficiency of siRNA,), this experiment compared non-treated cells (control) to cells treated with 50 nM free siRFP, and cells treated with a Lipofectamine (Invitrogen, USA)/siRFP complex in such an amount that siRFP was present at a concentration of 50 nM.

After incubation for 24 hrs, the cells were fixed in a fixation agent, and treated with a DAPI mounting solution to stain the nuclei. RFP fluorescence intensity was measured by fluorescence microscopy to evaluate the gene therapy efficacy of the complex.

Figure 8:
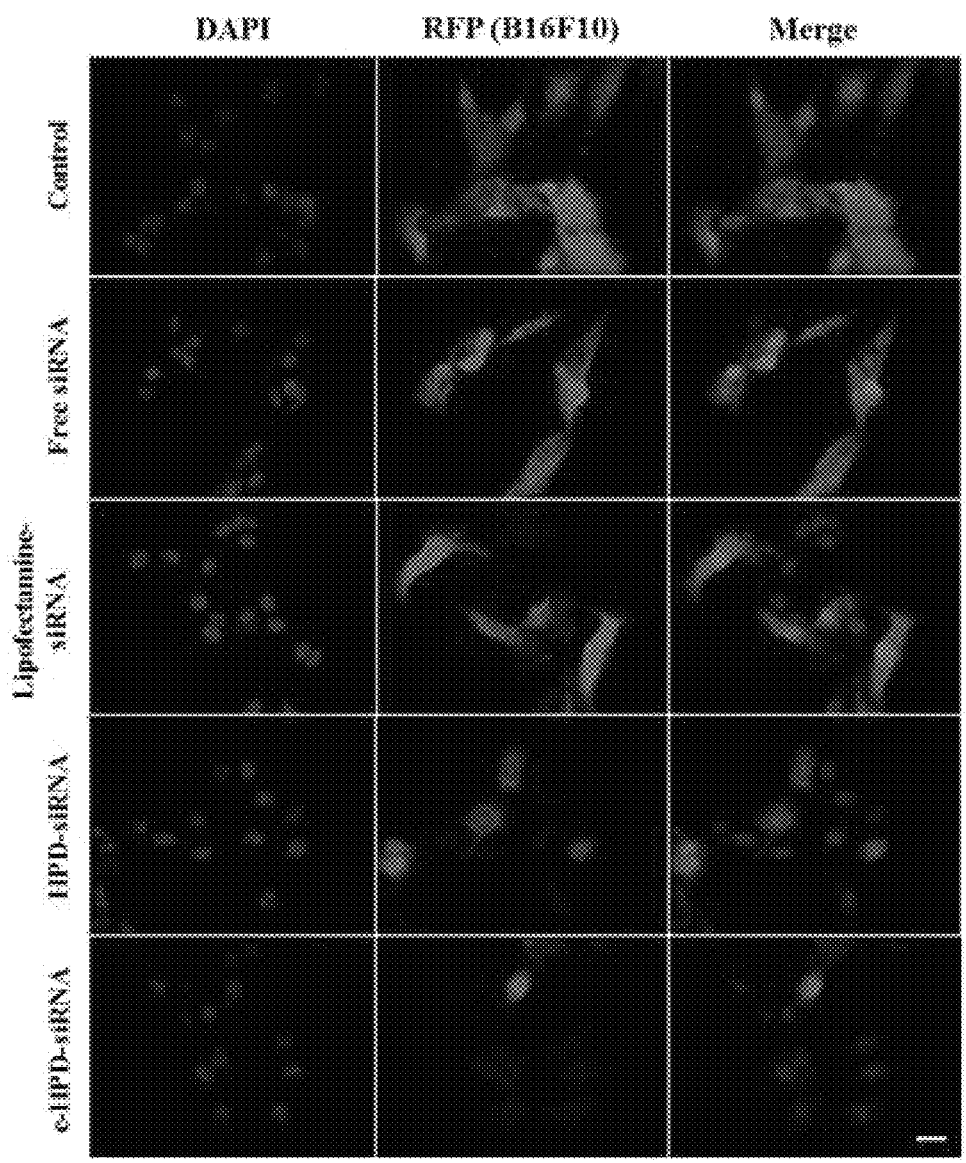
FIG. 8 displays fluorescent images showing changes in intracellular RFP fluorescence intensity by RFP gene silencing after treatment with a siRFP/HA-PDA-P(DMAEMA) complex, as measured by fluorescence microscopy.

The results are given in FIG. 8. In FIG. 8, c-HPD-siRNA refers to a complex of the HA-PDA-P(DMAEMA) conjugate with siRNA (siRFP), crosslinked in the presence of a reducing agent (DTT). FIG. 8 reveals a significantly low fluorescence intensity was detected in the cells treated with the siRFP/HA-PDA-P(DMAEMA) complex, compared to the non-treated cells, the free siRFP-treated cells, and the Lipofectamine)/siRFP complex-treated cells, indicating that the siRFP/HA-PDA-P(DMAEMA) complex delivered siRNA at a higher rate into cells, thereby effectively suppressing the expression of RFP.

In addition, the siRFP/HA-PDA-P(DMAEMA) complex is endocytosed selectively by cancer cells because the hyaluronic acid binds to CD44 receptors overexpressed on cancer cell surfaces, specifically and rapidly. Through this endocytosis process, the siRNA of the complex can be more effectively introduced into cells and can more effectively inhibit target proteins than can other conventional delivery system.

Example 10

Assay for in Vivo Distribution Behavior of siRFP-HPD and c-siRFP-HPD in Tumor Animal Model To evaluate the in vivo distribution behavior of the siRFP-HPD and the c-siRFP-HPD, a near-infrared fluorophore-labeled HPD was prepared, allowed to form a complex with siRFP, and administered into tumor animal models by intravenous injection, followed by monitoring distribution behaviors with time using a near-infrared fluorescence imaging apparatus.

First, HPD was labeled with a NIR fluorophore. To accomplish this, 0.1 mg of Flamma™ (FPR-675) fluorophore ($\lambda_{ex}$=675, $\lambda_{em}$=720, Bioacts, Incheon, Korea) was reacted with 10 mg of HPD in 10 mM phosphate buffer (pH 8.0) for 24 hrs. The reaction mixture was concentrated through a centrifugal filter (Ultracel®-3K, Millipore Irenand Ltd, Ireland) at 14000 rpm, and washed with distilled water. This filtration was repeated three times, and lypholization of the filtrate afforded fluorophore-labeled HPD as a blue powder (F-HPD).

Separately, $1\times10^6$ sarcoma cell carcinoma cells (SCC7 cells, ATCC, USA) were implanted into the left side of a 5-week-old male nude mouse (Balb/C nude, Narabiotech, Korea) by subcutaneous injection to prepare a tumor animal model.

When a tumor was grown to a size of 80-150 mm$^3$ in the tumor animal model, the siRFP-F-HPD complex or the c-siRFP-F-HPD complex (1 mg/ml F-HPD) was injected at a dose of 200 μl into the tail vein of the tumor animal model. The mice were imaged 1, 3, 6, 9, 24, and 48 hrs after the injection, using the NIR fluorescence imaging apparatus, eXplore Optix system (ART Advanced Research Technologies, Inc., Montreal, Canada).

Figure 11:
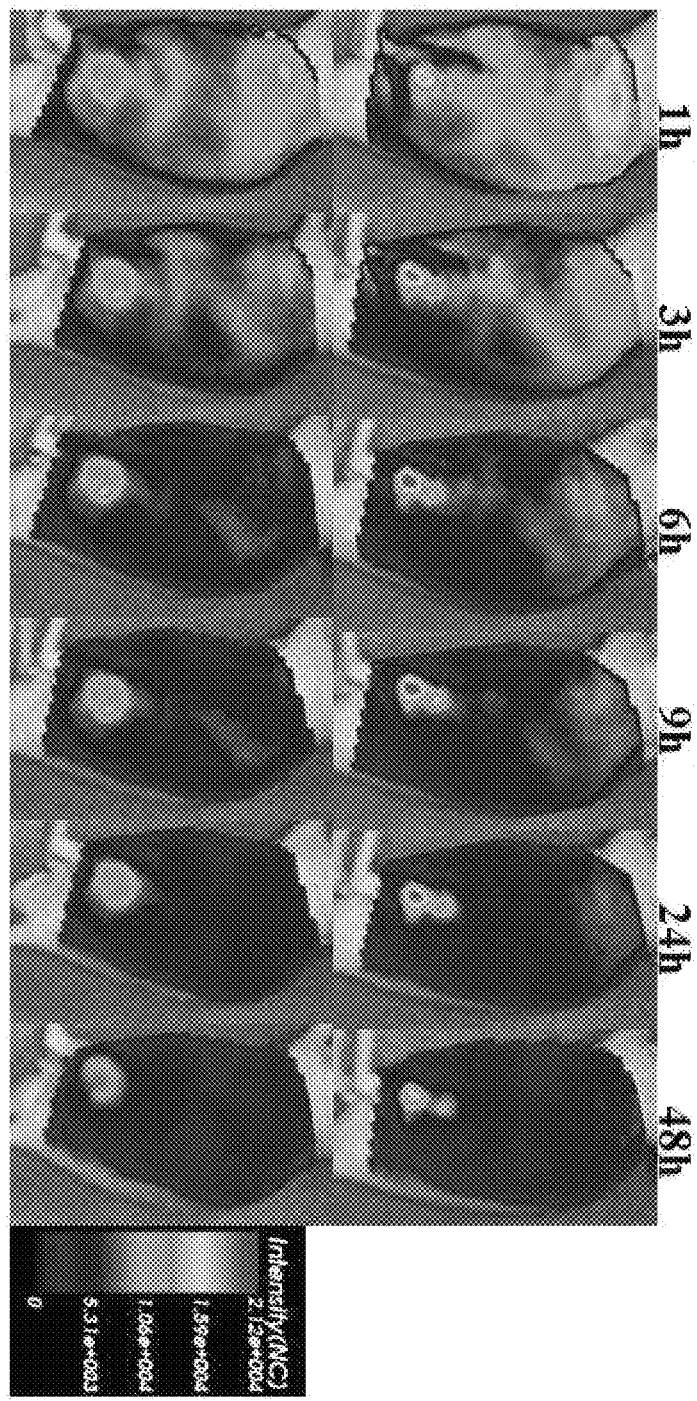
FIG. 11 displays near-infrared fluorescence images of tumor animal models in which fluorophore-labeled siRFP-HPD and c-siRFP-HPD are distributed at specific regions.
Figure 12:
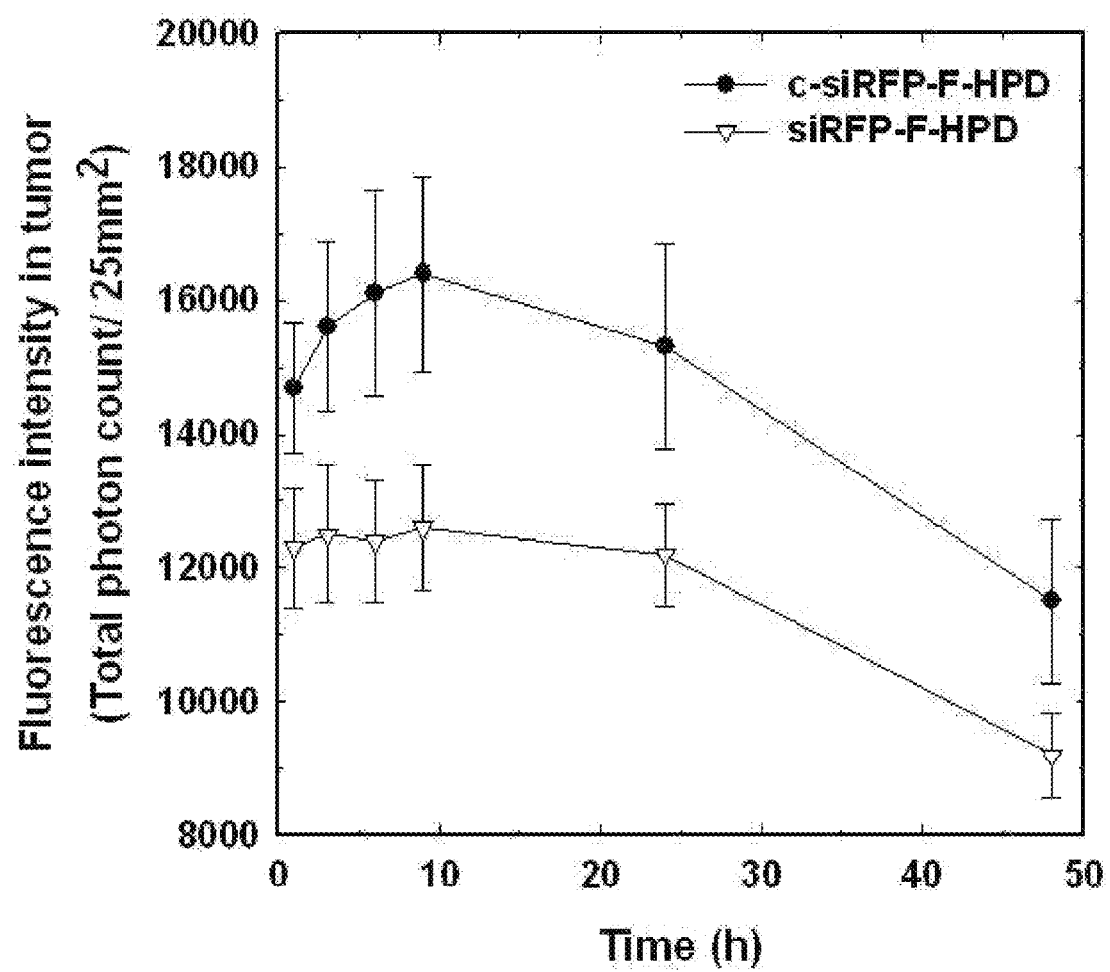
FIG. 12 is a graph in which the fluorescence intensity detected from the fluorescence images of FIG. 11 is quantified.

The NIR fluorescence images are given in FIG. 11. From these fluorescence images, fluorescence intensity around the tumor was quantitatively analyzed using Analysis Workstation software (ART Advanced Research Technologies, Inc., Montreal, Canada). The cumulative fluorescence intensity is plotted versus time in FIG. 12. As can be seen in FIGS. 11 and 12, both the siRFP-HPD complex and the c-siRFP-HPD complex according to a particular embodiment were found to have excellent cancer cell targeting ability. Moreover, higher cancer targeting ability and cumulativity were detected in the c-siRFP-HPD complex, indicating that the complex is greatly improved in morphological stability through crosslinkages.

These results demonstrate the siRNA-HPD and the c-siRNA-HPD complexes have the high ability to both target and accumulate in cancer cells in vivo, meaning they can effectively deliver nucleic acids into cancer tissues. Particularly, the c-siRNA-HPD complex, which is crosslinked, is predicted to be used as an excellent cancer-specific nucleic acid delivery system.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A hyaluronic acid conjugate, the conjugate comprising: hyaluronic acid, a disulfide bond-containing crosslinking agent, and a cationic, amphiphilic polymer,
   wherein 1 to 30 percent of the carboxyl groups of the hyaluronic acid are substituted with the disulfide bond-containing crosslinking agent, and 1 to 30 percent of the carboxyl groups of the hyaluronic acid are substituted with the cationic, amphiphilic polymer, and
   wherein the disulfide bond-containing crosslinking agent comprises pyridyldithioethylamine (PDA), succinimidyl 3-(2-pyridylthio)propionate (SPDP), succinimidyl 6-(3'-[2-pyridyldithio]-propionamido)hexanoate (LC-SPDP), sulfosuccinimidyl 6-(3'[2-pyridyldithio]-propionamido)hexanoate (Sulfo-LC-SPDP), 3,3'-dithiobis(sulfosuccinimidylpropionate) (DTSSP), or any combination thereof, and
   the cationic, amphiphilic polymer comprises dimethylaminoethyl methacrylate (DMAEMA), poly(dimethylaminoethyl methacrylate) (P(DMAEMA), chitosan, glycol chitosan, polyamidoamine dendrimer, or any combination thereof.

2. A self-assembling composition comprising a plurality of the hyaluronic acid conjugates of claim 1 crosslinked via disulfide bonds.

3. A hyaluronic acid-nucleic acid complex, the complex comprising:
   a hyaluronic acid conjugate, wherein the conjugate comprises a hyaluronic acid, a disulfide bond-containing crosslinking agent, and a cationic, amphiphilic polymer, wherein 1 to 30 percent of the carboxyl groups of the hyaluronic acid are substituted with the disulfide bond-containing crosslinking agent, and 1 to 30 percent of the carboxyl groups of the hyaluronic acid are substituted with the cationic, amphiphilic polymer; and
   a nucleic acid;
   wherein the nucleic acid is linked to the cationic, amphiphilic polymer of the hyaluronic acid conjugate, and
   wherein the disulfide bond-containing crosslinking agent comprises pyridyldithioethylamine (PDA), succinimidyl 3-(2-pyridylthio)propionate (SPDP), succinimidyl 6-(3'[2-pyridyldithio]-propionamido)hexanoate (LC-SPDP), sulfosuccinimidyl 6-(3'[2-pyridyldithio]-propionamido)hexanoate (Sulfo-LC-SPDP), 3,3'-dithiobis(sulfosuccinimidylpropionate) (DTSSP), or any combination thereof, and
   the cationic, amphiphilic polymer comprises dimethylaminoethyl methacrylate (DMAEMA), poly(dimethylaminoethyl methacrylate) (P(DMAEMA), chitosan, glycol chitosan, polyamidoamine dendrimer, or any combination thereof.

4. The hyaluronic acid-nucleic acid complex of claim 3, wherein the nucleic acid comprises RNA, DNA, siRNA, an aptamer, antisense ODN, antisense RNA, ribozyme, DNAzyme, or combination thereof.

5. The hyaluronic acid-nucleic acid complex of claim 3, wherein the weight ratio of the hyaluronic acid conjugate to the nucleic acid is from about 99:1 to about 5:95.

6. The hyaluronic acid-nucleic acid complex of claim 5, wherein the weight ratio of the hyaluronic acid conjugate to the nucleic acid is from about 5:1 to about 25:1.

7. A method for delivering a nucleic acid to a subject, the method comprising: administering the hyaluronic acid-nucleic acid complex of claim 3 to a subject in need thereof.

8. A self-assembling composition comprising a plurality of the hyaluronic acid-nucleic acid complexes of claim 3 crosslinked via disulfide bonds.

9. A method for delivering a nucleic acid to a subject, the method comprising administering the self-assembling composition of claim 8 to a subject in need thereof.

10. A method for preparing a hyaluronic acid conjugate comprising:
    (1) reacting a hyaluronic acid with a disulfide bond-containing, cationic, amphiphilic polymer; and
    (2) reacting the cationic, amphiphilic polymer-bound hyaluronic acid with a crosslinking agent to provide a hyaluronic acid conjugate,
    wherein 1 to 30 percent of the carboxyl groups of the hyaluronic acid are substituted with the disulfide bond-containing crosslinking agent, and 1 to 30 percent of the carboxyl groups of the hyaluronic acid are substituted with the cationic, amphiphilic polymer, and wherein the disulfide bond-containing crosslinking agent comprises pyridyldithioethylamine (PDA), succinimidyl 3-(2-pyridylthio)propionate (SPDP), succinimidyl 6-(3'-[2-pyridyldithio]-propionamido)hexanoate (LC-SPDP), sulfosuccinimidyl 6-(3'[2-pyridyldithio]-propionamido)hexanoate (Sulfo-LC-SPDP), 3,3'-dithiobis(sulfosuccinimidylpropionate) (DTSSP), or any combination thereof, and the cationic, amphiphilic polymer comprises dimethylaminoethyl methacrylate (DMAEMA), poly(dimethylaminoethyl methacrylate) (P(DMAEMA), chitosan, glycol chitosan, polyamidoamine dendrimer, or any combination thereof.

* * * * *

SEQUENCE LISTING

<160> NUMBER OF SEQ ID NOS: 2

<210> SEQ ID NO 1
<211> LENGTH: 19
<212> TYPE: RNA
<213> ORGANISM: Artificial Sequence
<220> FEATURE:
<223> OTHER INFORMATION: Synthetic (sense strand of siRNA against
      RFP (siRFP))

<400> SEQUENCE: 1
uguagaugga cuugaacuc                                              19

<210> SEQ ID NO 2
<211> LENGTH: 19
<212> TYPE: RNA
<213> ORGANISM: Artificial Sequence
<220> FEATURE:
<223> OTHER INFORMATION: Synthetic (antisense strand of siRNA against
      RFP (siRFP))

<400> SEQUENCE: 2
gaguucaagu ccaucuaca                                              19